(12) United States Patent
Meredith et al.

(10) Patent No.: US 8,235,619 B2
(45) Date of Patent: Aug. 7, 2012

(54) CONTAINER FOR SEQUENTIALLY DISPENSING MULTIPLE FLUIDS ONTO AN APPLICATOR DEVICE

(75) Inventors: William R. Meredith, Raleigh, NC (US); Annette Johnson Meredith, Raleigh, NC (US); Albert J. Parvin, San Antonio, TX (US); Erika C. Laiche, San Antonio, TX (US)

(73) Assignees: William R. Meredith, Raleigh, NC (US); Annette Johnson Meredith, Raleigh, NC (US)

( * ) Notice: Subject to any disclaimer, the term of this patent is extended or adjusted under 35 U.S.C. 154(b) by 266 days.

(21) Appl. No.: 12/782,680

(22) Filed: May 18, 2010

(65) Prior Publication Data

US 2011/0121030 A1    May 26, 2011

Related U.S. Application Data

(60) Provisional application No. 61/179,190, filed on May 18, 2009.

(51) Int. Cl.
 *B05C 17/01* (2006.01)
(52) U.S. Cl. ........ 401/171; 401/195; 422/292; 422/297; 422/298
(58) Field of Classification Search .................. 401/170, 401/195; 422/292, 297, 298, 26
See application file for complete search history.

(56) References Cited

U.S. PATENT DOCUMENTS

| 4,585,119 | A | 4/1986 | Boyington |
|---|---|---|---|
| 5,023,460 | A | 6/1991 | Foster, Jr. et al. |
| 5,882,613 | A | 3/1999 | Gipson, II |
| 6,099,813 | A | 8/2000 | Gipson, II |
| 6,565,819 | B1 | 5/2003 | Herrera |
| 7,451,514 | B2 | 11/2008 | Blaustein et al. |
| 2004/0155201 | A1 | 8/2004 | Russell et al. |
| 2006/0204416 | A1 | 9/2006 | Hayes et al. |
| 2007/0251040 | A1 | 11/2007 | Braun et al. |
| 2008/0118300 | A1 | 5/2008 | Burrowes |
| 2008/0219883 | A1 | 9/2008 | Thur et al. |

*Primary Examiner* — Tuan N Nguyen
(74) *Attorney, Agent, or Firm* — Kammer Browning PLLC

(57) ABSTRACT

A structure and system are described which include the use of a combination container for sequentially dispensing multiple fluids onto a removable applicator device. A preferred application of the invention is with the sequential dispensing of a quantity of disinfecting solution over a toothbrush, followed by the dispensing of a measured quantity of toothpaste onto the toothbrush. The device is constructed in a double walled cylindrical (circular or non-circular) configuration with a hollow plunger component coaxially positioned within the cylindrical walls. Beneath the plunger component is contained a quantity of disinfectant solution such that when the plunger is directed downward the disinfectant solution is forced upward between the walls of the double walled container and through dispensing ports directed into the interior where the applicator is positioned. The contained motion of the plunger component downward under the directed force of the applicator brings the base of the hollow plunger into contact with the base wall of the container and causes the collapse of the hollow plunger. A second liquid/gel contained within the hollow plunger is then directed up and out of its enclosed volume through ports aligned with the applicator. The design is intended to accommodate a wide variety of compounds and applicators. Wherever the dispensing of two different compounds (liquids/gels) is required in a sequential manner, the present invention finds applicability.

1 Claim, 8 Drawing Sheets

CONTAINER FOR SEQUENTIALLY DISPENSING MULTIPLE FLUIDS ONTO AN APPLICATOR DEVICE

CROSS REFERENCE TO RELATED APPLICATIONS

This application claims the benefit under Title 35 United States Code §119(e) of U.S. Provisional Application 61/179,190 filed May 18, 2009, the full disclosure of which is incorporated herein by reference.

BACKGROUND OF THE INVENTION

1. Field of the Invention

The present invention relates generally to container systems for holding and dispensing fluids, especially for dispensing fluids and/or gels onto an applicator. The present invention relates more specifically to a container system for sequentially dispensing multiple fluids and/or gels onto an applicator. The present invention finds specific application to a container system for disinfecting a toothbrush with a disinfectant liquid and subsequently dispensing a quantity of toothpaste onto the toothbrush for use.

2. Description of the Related Art

There are many activities that involve the dispensing of a compound, such as a fluid or a gel onto an applicator, such as a brush, for subsequent application to some external surface or object. In most cases where only a single fluid or gel is utilized the container dispensing system can be relatively straight forward and simple. The primary requirement in such cases is that the user be able to generally control the quantity of compound that is being dispensed. A second requirement is that the fluid or gel be accurately dispensed onto the appropriate part of the applicator to optimize the process of applying the fluid or gel to the external surface.

Some activities involve the use and dispensing of multiple distinct compounds, such as fluids or gels onto or over an applicator, such as a brush, in sequence in such a manner as to gain the benefits associated with the functionality of each of the compounds dispensed. In some cases two compounds are dispensed (either together or in sequence) in order to combine and create a chemical reaction that results in a new compound that is then applied using the applicator to some external surface or the like. A typical example of such use of an applicator to apply two dispensed and combined compounds would be a two part epoxy resin adhesive.

With other activities it is necessary to dispense a first compound onto or over the applicator, such as for the purpose of cleansing the applicator, prior to dispensing a second compound onto the applicator, the second compound then used by being applied to some external surface. The present invention addresses applications of each of the above described activities, those where two compounds are dispensed onto an applicator for use together (such as through a chemical reaction to form a single new compound) and those where it is necessary to apply a first compound to the applicator for the purposes of preparing the applicator in some manner for the subsequent receipt of the second compound.

Although the present invention is directed generally to combinations of multiple compounds being dispensed onto an applicator, provided herein are descriptions of a toothbrush with toothpaste and a toothbrush disinfectant, as perhaps a primary example of the use of the fundamental concepts of the invention. It is known, for example, that it is beneficial to disinfect a toothbrush prior to use. Various disinfecting liquids are known in the art as are a variety of different disinfecting containers. Most of these systems provide a container into which a toothbrush may be immersed for a period of time before being removed and subsequently provided with toothpaste from a separate container. Other known approaches to toothbrush decontamination include ultra-violet (UV) light based systems that subject the toothbrush to the known disinfecting qualities of UV light.

In addition to the above described disinfectants, a variety of toothpaste dispensing devices, both those directly associated with toothbrushes and those configured apart from toothbrushes, are known in the art. There are, for example, a variety of toothbrush configurations that include within the handle of the brush reservoirs for both disinfectant liquids and toothpaste. Most such toothbrushes that contain toothpaste that may be dispensed onto the toothbrush bristles are disposable configurations and are not intended to be reused after having dispensed the limited quantity of toothpaste contained therein. For the most part, the current state of the art in the tooth brushing field provides for separate disinfecting containers (that may or may not be refillable with additional disinfecting fluids) that are used in conjunction with reusable toothbrushes that are then used with conventional toothpaste dispensers, to provide the user with the standard quantity and type of toothpaste for brushing their teeth.

Because it is desirable to utilize both toothbrush disinfecting solutions and, subsequent thereto, toothpaste compositions, it would be desirable to provide for the combined process or sequence of steps in association with a single device or an automated dispensing system.

The present invention therefore finds as its primary objectives: (1) combining devices that provide disinfecting solutions to a toothbrush with devices that provide toothpaste to the bristles on a toothbrush immediately prior to use; (2) providing an automated means of dispensing measured quantities of both the disinfecting solution and the toothpaste composition onto or over the toothbrush; (3) providing a dispensing system that serves also as a containment system for the two liquids/gels associated with the process of brushing teeth; (4) providing a system that is easy and inexpensive to manufacture such that it may be manufactured in multiple disposable units subject to one time use in addition to a partially reusable or fully reusable embodiment of the system; and (5) providing for a variety of specialized configurations of the disinfectant and toothpaste dispensing system that may be in a decontaminated state or a partially sterile state and/or which may be configured for use during travel. Other objectives of the present invention will become apparent to those skilled in the art upon an understanding of the structures and functions of the components and assemblies as described in detail herein below.

SUMMARY OF THE INVENTION

In fulfillment of the stated objectives, the present invention provides a combination container for sequentially dispensing multiple fluids onto an applicator device. The invention finds perhaps its best use in conjunction with the sequential dispensing of a quantity of toothbrush disinfecting solution onto or over a toothbrush, followed by the dispensing of a measured quantity of toothpaste (or other dentifrice compound) onto the bristles of the toothbrush. The basic device designed to contain and dispense the two liquids/gels is constructed with a double walled cylindrical (circular or non-circular) configuration with a hollow plunger component positioned within the interior cylindrical walls of the device. Beneath the plunger component is contained a quantity of disinfectant solution such that, when the plunger is directed downward (into the container, as for example, by insertion of the applicator brush) the disinfectant solution is forced upward through channels positioned between the walls of the double walled container, and then through dispensing ports directed into the interior of the device where the applicator (the toothbrush, for example) is positioned. The applicator (brush) is preferably utilized to manually direct this downward motion of the plunger into the cartridge body whereby the liquids/gels are sequentially dispensed onto the applicator as it moves.

This dispensing of the first liquid/gel onto or over the brush applicator achieves the first functionality (disinfecting) with the applicator device. Movement of the plunger component downward under the directed force of the applicator (toothbrush) brings the base of the hollow plunger into contact with the inside bottom wall of the container. Continued force downward causes the collapse of the hollow plunger, which has been filled with a second liquid/gel (toothpaste) that is now directed up out of its enclosed volume through ports on an upper portion of the hollow plunger that are aligned with the tips of the bristles on the brush of the applicator.

This two stage process anticipates the separate containment of a first liquid/gel beneath the plunger in such a manner that movement of the plunger (Stage A) directs the first liquid up and through the appropriately positioned ports onto the applicator. Stage B of the process which continues the downward force on the hollow plunger, collapses the hollow plunger, within which has been contained the second liquid/gel, forcing it from the collapsing hollow plunger and directing it onto the brush components of the applicator.

As indicated above, the design of the present invention is intended to accommodate a wide variety of compounds and applicators. Wherever the dispensing of two different compounds (liquids/gels) is required in a sequential manner, the present invention finds particular applicability. Other applications of the present invention will be apparent to those skilled in the art upon a consideration of the drawing figures attached and the detailed description of the preferred embodiments set forth below.

DETAILED DESCRIPTION OF THE PREFERRED EMBODIMENTS

The present invention may generally be described as a system for sequentially dispensing two different liquids/gels onto or in association with an applicator. The detailed description that follows is directed to but one area of application (dental hygiene) appropriate for the basic functionality of the system. Other areas of application are anticipated and will be recognized by those skilled in the art from an understanding of the functionality of the system as described in the field of dental hygiene. Within the field of dental hygiene, there are described herein three specific user applications of the system. Each of the described systems involves the same basic application, namely the sequential dispensing of a disinfectant solution and a dentifrice (toothpaste or gel) onto or in association with an applicator (toothbrush). The first and likely the most commonly used device package, is a basic "consumer cartridge" embodiment. The second is a more highly decontaminated package referred to as the "specialty cartridge" that includes a pre-packaged and enclosed applicator (toothbrush). The third embodiment described is a compact package referred to as the "travel cartridge" that includes a two piece applicator (toothbrush). Each of the embodiments includes a lower cartridge body and a cartridge body top as generally described below. The consumer cartridge, however, will not include an enclosed toothbrush and will typically be manufactured with the cartridge body top attached directly to the open end of the cartridge body. The specialty cartridge and the traveler cartridge will each be manufactured with inserts between the open end of the cartridge body and cartridge body top, and each will be manufactured with an included toothbrush. Once again, the descriptions of three specific embodiments of the present invention within the dental hygiene field are not intended to be limiting of the invention to these three applications within the field, or even to the dental hygiene field as a whole. Rather, these descriptions are intended to provide details of the basic functionality of the system utilizing the present invention and to teach the manner in which these basic concepts may be applied to any of a number of different fields and different problems within those fields associated with the sequential dispensing of two liquid/gel compounds in association with an applicator.

Figure 1A:
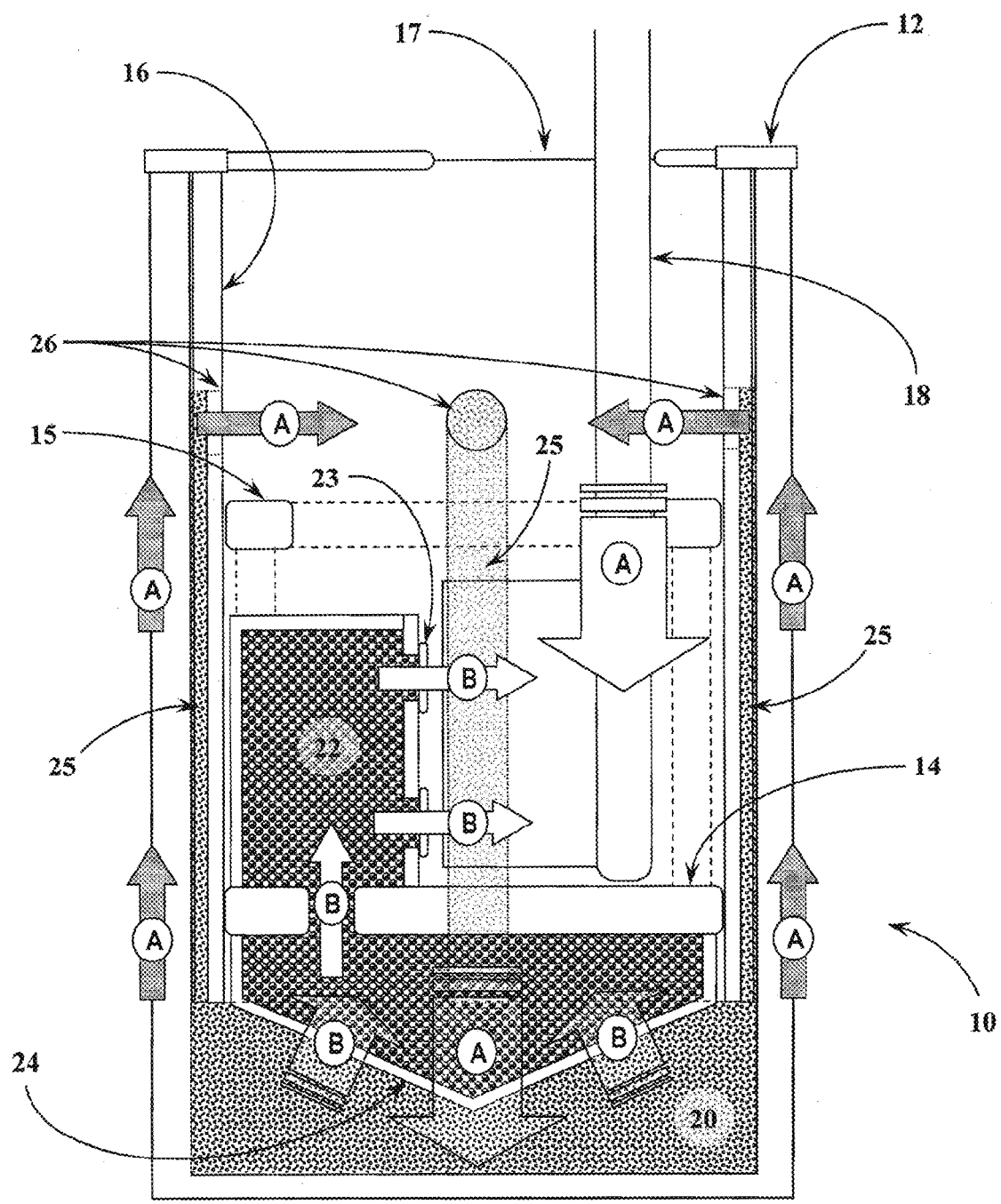
FIG. 1A is a schematic diagram showing the essential components of the container/cartridge system of the present invention as well as the functional flow of the first and second liquid/gels as they are dispensed onto the applicator.

Reference is made first to FIG. 1A for a detailed description of the basic structure and function of the container/cartridge device of the present invention. As will be recognized after a consideration of the subsequent figures in the present application, some details regarding the functional characteristics of the invention are difficult to disclose and describe in combination with the actual scaled structural configurations of the device. FIG. 1A is therefore presented as a schematic diagram indicating the basic structural relationships between the various components of the device, as well as to provide a clear representation of the flow of the fluids within the device upon activation. FIG. 1A is a schematic diagram of a cross-sectional view along an elevational profile of the container/cartridge that to some extent disregards the actual geometry and spacing of the components.

In the view disclosed in FIG. 1A, container/cartridge 10 is shown to be essentially constructed of housing 12 and plunger body 14. Plunger body 14 is a generally cylindrical structure which movably fits within the cylindrical structure of dispensing cylinder 16 which is coaxially positioned within housing 12. The space between the walls of dispensing cylinder 16 and housing 12 is exaggerated in this view for clarity. Although in the preferred embodiment described herein the container/cartridge 10, housing 12, and plunger body 14 are described as cylindrical (circular in cross-section), it is anticipated that other cross-sectional configurations (such as square or rectangular) might be implemented. A rectangular cross-section for example, would accept a toothbrush type applicator while also saving storage space (as when a package of cartridges is bundled together side by side).

Initially contained in a volume below and outside of plunger cap 24, is a first liquid/gel 20. Plunger body 14 has as its base plunger cap 24 which is a deformable cover or wall that encloses a quantity of a second liquid/gel 22 as shown. The system is therefore designed to direct the flow of the first liquid/gel 20 up into channels 25 positioned within an annular space between housing 12 and dispensing cylinder 16 upon the direction of plunger body 14 downward into the volume defined by housing 12. In the preferred embodiment, channels 25 are scored into the outer walls of dispensing cylinder 16 from its base up to dispensing ports 26.

Plunger body 14 is, as mentioned above, further constructed of walled elements that define pathways for the flow of second liquid/gel 22 up from the deformable compartment defined by plunger cap 22 and eventually out onto applicator 18. First liquid/gel 20 is directed to be sprayed onto applicator 18 by way of the first liquid/gel dispensing ports 26 positioned in an elevated location on dispensing cylinder 16. As plunger body 14 and applicator 18 descend into dispensing cylinder 16, first liquid/gel 20 is sprayed onto applicator 18 as its bristles pass by dispensing ports 26. Subsequent thereto, second liquid/gel 22 is directed to be dispensed into the bristles of applicator 18 through the ports shown in the structured top surface walls of plunger body 14. In the preferred embodiment, the ports through which second liquid/gel 22 is directed are initially sealed over with burst disc seals 23 which burst when second liquid/gel 22 is forced out from the plunger enclosures. In this manner second liquid/gel 22 is prevented from leaking from the dispensing ports and is further prevented from drying out, hardening, or becoming contaminated by contact with the atmosphere.

The operation of the system as shown in FIG. 1A is essentially a two-stage process whereby the first and second liquid/gels are sequentially directed onto or into the bristles of applicator 18. Applicator 18 is initially introduced into the interior of dispensing cylinder 16 through applicator portal 17, within the confines of halo stabilizer 15, and onto the top of plunger body 14 where it comes into contact with the upper structures associated with plunger body 14 (described in more detail below). This insertion of applicator 18 and the exertion of a downward force on applicator 18, directs plunger body 14 downward (Stage A) in the dispensing cylinder 16 and serves to displace a quantity of first liquid/gel 20 contained within the base of housing 12. Wide arrows shown in FIG. 1A represent the forces and the direction of such forces (labeled Stage A and Stage B) during activation of the container/cartridge 10, whereas narrow arrows are shown to indicate the flow of fluids (labeled Stage A and Stage B) that result from the activation of the forces shown.

The system shown in FIG. 1A as described above is divided into Stage A and Stage B identified on each of the force arrows and flow arrows. Stage A initially involves the exertion of downward pressure on plunger body 14 in a manner that directs it into the quantity of first liquid/gel 20 that is contained within housing 12 as described above. The reduction in the space available to first liquid/gel 20 near the base of housing 12 forces it to rise (flow arrows A) upward into the channels 25 positioned within the annular space between housing 12 and dispensing cylinder 16. As soon as first liquid/gel 20 rises to the level of first liquid/gel dispensing ports 26 it is forced into the interior of dispenser cylinder 16 where it is dispensed (sprayed) over and around applicator 18.

As a downward force continues to be exerted on applicator 18, thereby directing plunger body 14 all the way to the bottom of housing 12, plunger cap 24 comes into physical contact with the bottom (interior wall) of housing 12 and begins to deform under the forces (force arrows B) as shown. This causes the volume within which the second liquid/gel 22 is contained within plunger cap 24 to collapse and therefore force second liquid/gel 22 upward from this separate lower volume through a connecting conduit to a dispensing portion of plunger body 14. From this dispensing portion of plunger body 14, second liquid/gel 22 is directed through the dispensing ports (breaking burst disc seals 23) as indicated (flow arrows B) and into the bristles of applicator 18. It is then anticipated that the applicator 18, having been first washed with first liquid/gel 20, and subsequently having had second liquid/gel 22 dispensed into its bristles, may be removed and utilized to gain the benefit of the liquids thus dispensed.

The representation in FIG. 1A is intended to be generic with respect to the liquids/gels that are being dispensed, as well as generic with respect to the applicator that is utilized to dispense and receive these liquids/gels. The following descriptions more specifically address a first preferable application of the present invention to a specific applicator and specific liquids/gels. Those skilled in the art will recognize that modifications to the structures shown in the following diagrams can easily be made that still adhere to the basic concepts set forth and described in association with FIG. 1A.

Figure 1B:
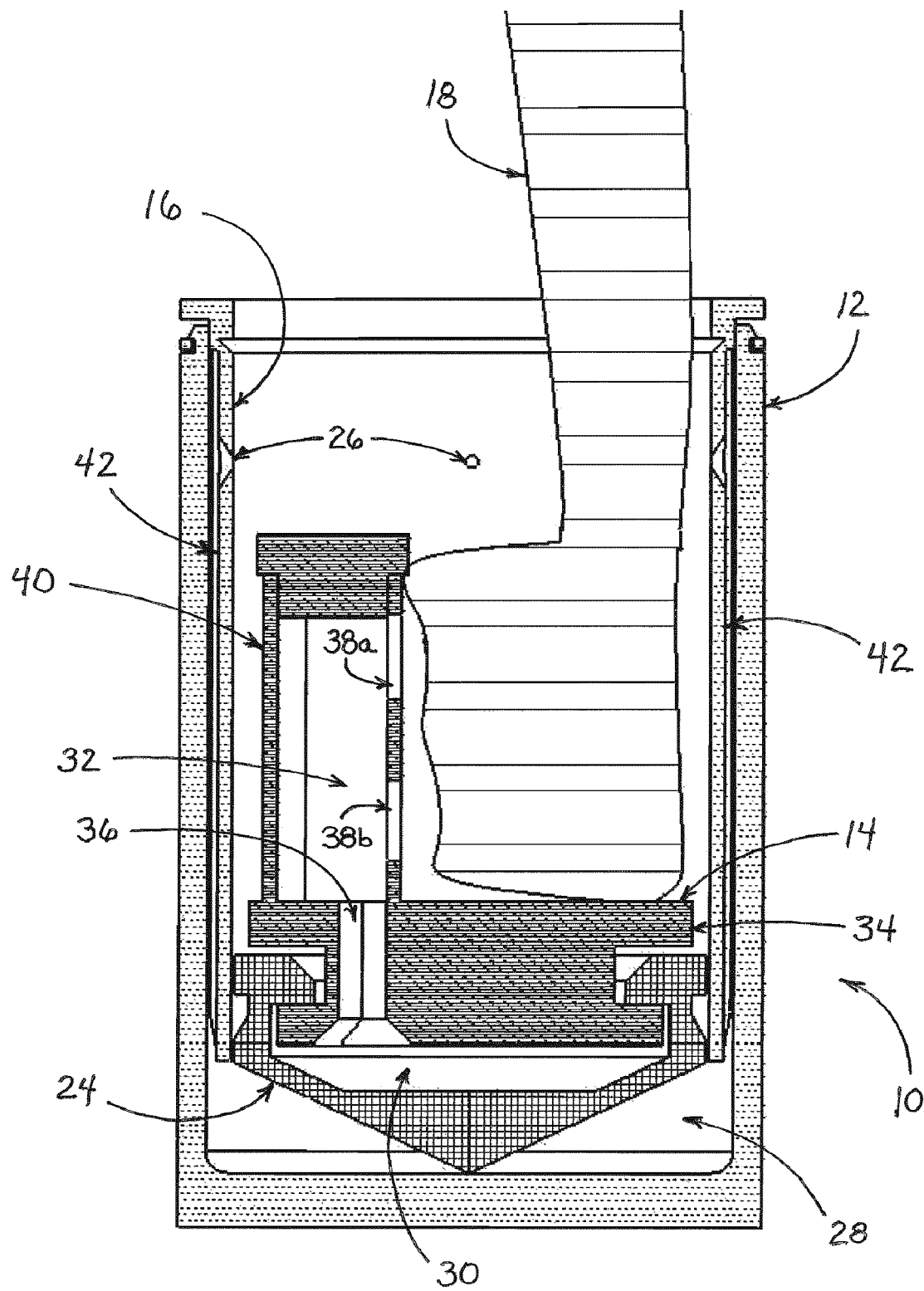
FIG. 1B is a cross-sectional view of a first embodiment of the present invention configured for use in conjunction with a toothbrush (as the applicator), a liquid disinfectant (as the first liquid/gel), and toothpaste (as the second liquid gel).

FIG. 1B provides essentially the same view as that shown in FIG. 1A, but as a cross-sectional view of a structure specifically designed for use in conjunction with a toothbrush, a toothbrush disinfectant liquid, and a toothpaste gel. FIG. 1B shows container/cartridge 10 as comprising housing 12 and plunger body 14. Toothbrush 18 is directed through an opening into the interior space defined by dispensing cylinder 16 which is coaxially positioned within housing 12. First liquid/gel 20 and second liquid/gel 22 are omitted in this view for clarity. Instead, disinfectant volume 28 is shown positioned below plunger cap 24 associated with plunger body 14. First toothpaste volume 30 is shown in place of a portion of the second liquid/gel 22 previously shown in FIG. 1A. Second toothpaste volume 32 is shown as defining a second portion of the volume previously occupied by second liquid/gel 22 shown in association with the second liquid/gel dispensing ports shown generally in FIG. 1A.

Plunger cap 24 in the embodiment shown in FIG. 1B fits in association with plunger top 34 to make up the base of plunger body 14. Extending above and integral with plunger top 34 is toothpaste dispenser riser 40 described generally above as containing the toothpaste dispensing ports. Connecting first toothpaste volume 30 with second toothpaste volume 32 is toothpaste conduit 36 which, in the preferred embodiment, may likewise be filled with toothpaste and simply serve to conduct as much toothpaste as is possible from first toothpaste volume 30 positioned within the flexible plunger, into second toothpaste volume 32 positioned within toothpaste dispenser riser 40 where it may be dispensed through toothpaste ports 38a and 38b onto toothbrush 18. Once again, in the preferred embodiment, bust disc seals may be positioned over ports 38a and 38b to seal the ports prior to use. It is noted that toothbrush 18 shown in a profile configuration in FIG. 1B comprises a handle portion and a bristle brush portion into which the toothpaste is dispensed, the structure of which is as may be known in the art.

Once again, disinfectant volume 28 is shown to be in flow conduction with dispensing ports 26 through channels 42 positioned in the annular space between housing 12 and dispensing cylinder 16. In this manner, the disinfectant contained within disinfectant volume 28 may be forced upward into channels 42 and thereafter through ports 26 to spray toothbrush 18 with the disinfectant solution.

When toothbrush 18 continues its downward motion past the first step (Stage A) of dispensing disinfectant solution onto the toothbrush by the manner described above, the plunger cap 24 contacts the base of housing 12 (the interior wall thereof) and begins to deform, thereby decreasing the volume of first toothpaste volume 30. This forces toothpaste contained within the volume up through toothpaste conduit 36 and likewise directs any toothpaste contained in second toothpaste volume 32 outward through toothpaste ports 38a and 38b as described above.

Figure 2:
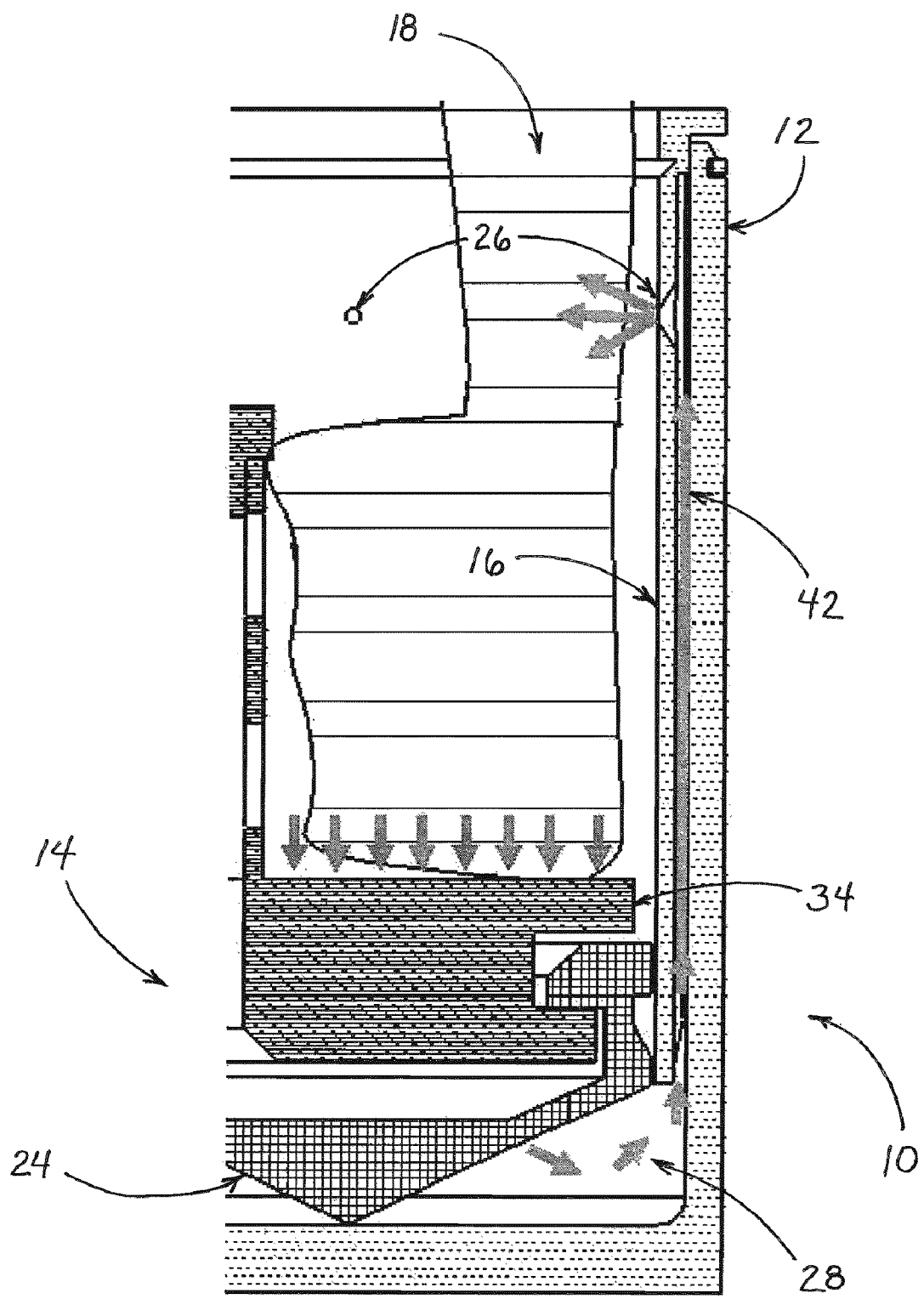
FIG. 2 is a cross-sectional view showing in greater detail the initial flow (Stage A) of a first fluid/gel (disinfectant) upon activation of the device of the present invention.
Figure 3:
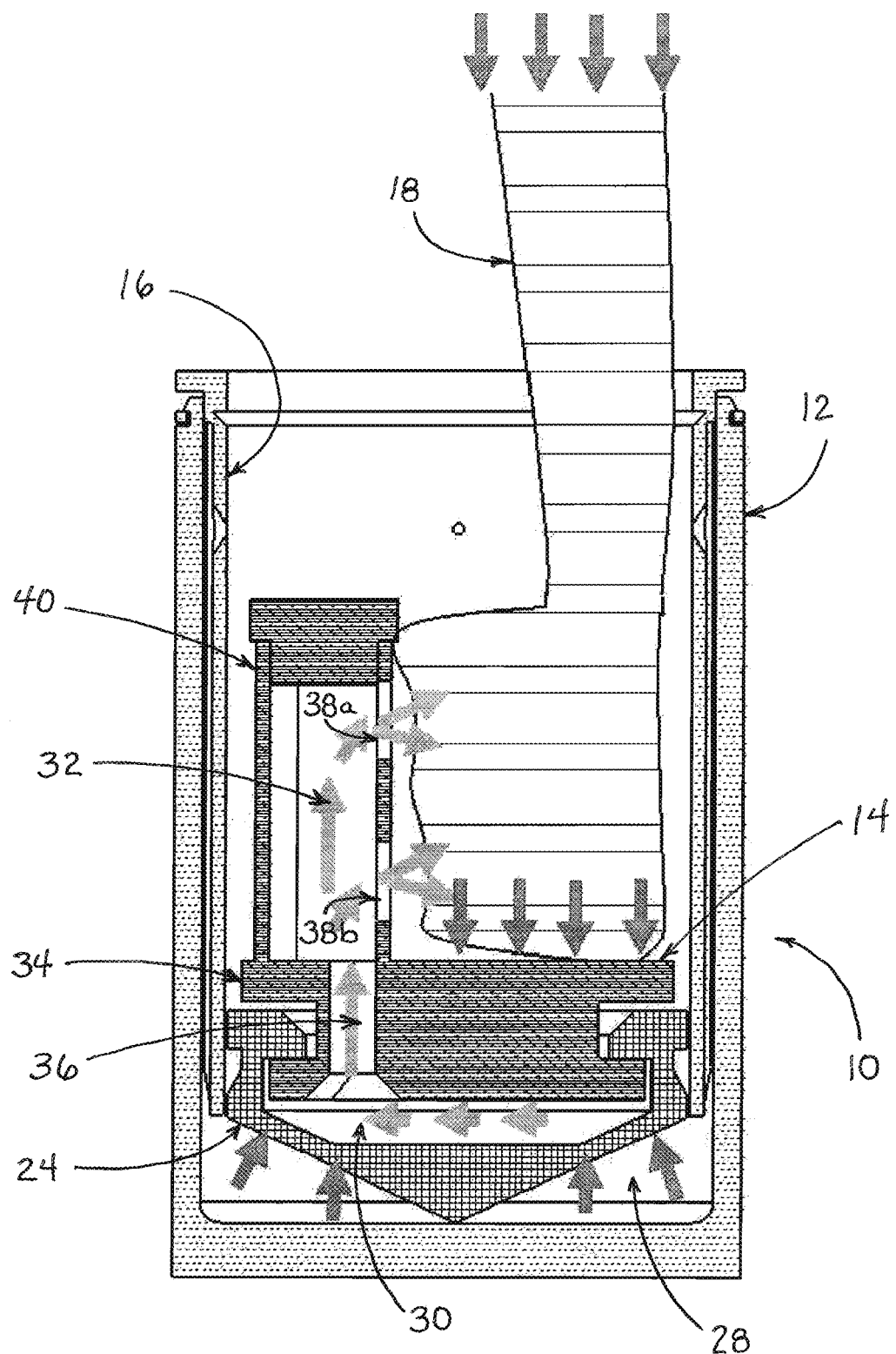
FIG. 3 is a cross-sectional view showing in greater detail a subsequent flow (Stage B) of a second fluid/gel (toothpaste) upon continued activation of the device of the present invention.

Reference is now made to FIG. 2 for a brief description of the manner in which the initial motion of directing toothbrush 18 downward into the center of dispensing cylinder 16 to contact plunger body 14 and to activate the container/cartridge 10 is carried out. FIGS. 2 and 3 are intended to show in greater detail the manner in which the first and second liquids/gels (through Stages A and B) are directed to flow from their place of containment onto or over the applicator that is directed into the container/cartridge. In the example described herein (a toothbrush with disinfectant and toothpaste) the toothbrush 18 is initially directed into the interior space of dispensing cylinder 16. As shown in FIG. 2 the applicator end (in this case, the end of the toothbrush that bears the bristles) is directed into contact with plunger top 34 as shown. Initially, this force (shown by the first set of arrows) moves plunger body 14 downward into housing 12 in a manner that forces the displacement of the disinfectant from disinfectant volume 28 into the channels 42 within the annular space between dispensing cylinder 16 and housing 12. When this disinfectant (shown by the second set of arrows in FIG. 2) reaches ports 26 it is directed under pressure through these ports over toothbrush 18 as it moves past the ports while directing the plunger downward into the cartridge body. There is sufficient free volume within the enclosure of dispensing cylinder 16 to receive and retain any excess disinfectant fluid that might flow over toothbrush 18 as it carries out its disinfecting functionality.

The orientation of the device of the present invention during use is critically important. A generally vertical orientation of the cylindrical device is required so as to evenly distribute the first liquid/gel through each of the spaced apart channels and dispensing ports. The more the device is tilted, the more the reservoir will favor one or more channels and nozzles (ports). Ultimately, an excessive tilt from the vertical could result in air/gas moving through the channel inlets rather than the liquid/gel as intended. The quantity of the first liquid/gel that comes in contact with the applicator bristles is therefore dependent on a proper vertical orientation of the device during use. In a preferred use of the system, therefore, the user would first place the base of the device on a solid counter top or other horizontal surface before inserting the toothbrush applicator.

As soon as plunger body 14 (and in particular plunger cap 24) reaches the full extent of its downward motion, it comes into contact with the interior wall of the base of housing 12. This begins the process of deforming plunger cap 24 in a manner that reduces the first toothpaste volume 30 as described above. In the process, however, the deforming of plunger cap 24 serves to force outward the last remaining amount of disinfectant found within disinfectant volume 28 as shown with the flow arrows in FIG. 2.

FIG. 3 provides an indication of the fluid flow and forces associated with the second stage (Stage B) of the operation of container/cartridge 10 of the present invention. After plunger body 14 has reached its full extent of being directed into housing 12 and plunger cap 24 has come into contact with the interior wall of the base of housing 12, plunger cap 24 begins to deform and thereby reduce first toothpaste volume 30 thereby initiating the flow of toothpaste out from the desired containment volumes. Force arrows shown in FIG. 3 within disinfectant volume 28 identify the manner in which the upward forces resulting from contact with the interior wall of base housing 12 direct the deformation of plunger cap 24 and thereby initiate the directed flow of toothpaste from first toothpaste volume 30. As indicated above, this quantity of toothpaste is directed to flow through toothpaste conduit 36 into second toothpaste volume 32 defined by toothpaste dispenser riser 40. The only outlet for this directed (pressurized) flow is through toothpaste ports 38a and 38b as shown. The toothpaste directed outward from these ports (after breaking the burst disc seals in the preferred embodiment) is directed into the brush or bristle portion of toothbrush 18 as described above.

The dispensing of each of the two liquids/gels in the sequential two step process described above is accomplished solely through the motion and directed force of toothbrush 18 downward into the center volume of dispensing cylinder 16 and the contact with plunger body 14. The arrangement of the components of the system allow for the discreet and sequential dispensing of the two fluids as described and as would be required for appropriate two step use of the system. That is, it is important that the disinfectant be initially dispensed over the toothbrush 18 so as to eliminate or reduce the quantity of bacteria, pathogens, or other microorganisms on the brush prior to the placement of toothpaste onto the brush, all prior to use by the individual using the container/cartridge.

The system of the present invention may be manufactured according to known processes for molding and milling the predominantly plastic components of the system. In a preferred method of manufacturing, when the device is loaded and assembled at a factory, the plunger assembly would preferably be positioned (for distribution and sale of the product) inside the cylinder in such a way that the rinse spray nozzles are covered and sealed off by the tight fitting plunger material. This is an important manufacturing step as without positioning the plunger in this manner the liquid rinse could potentially leak out through the nozzle openings with only a slight change in atmospheric pressure. In addition, it should be noted that the air or inert gas contained between the plunger and the rinse reservoir is slightly compressed as the plunger is forced downward for the first several thousandths of an inch. Once the plunger passes and therefore opens the nozzles to the passing brush, the compressed air or inert gas will be allowed to expand to its original volume such that the liquid will begin to spray at an initially higher velocity than will be the case through the remainder of the rinse cycle. The incompressibility of the rinse means that the gas/air component will serve as a type of "shock absorber" during the initial stage of the applicator insertion, and that the cylinder should preferably not be filled completely with rinse solution, as this could cause a failure of the device.

Figure 4:
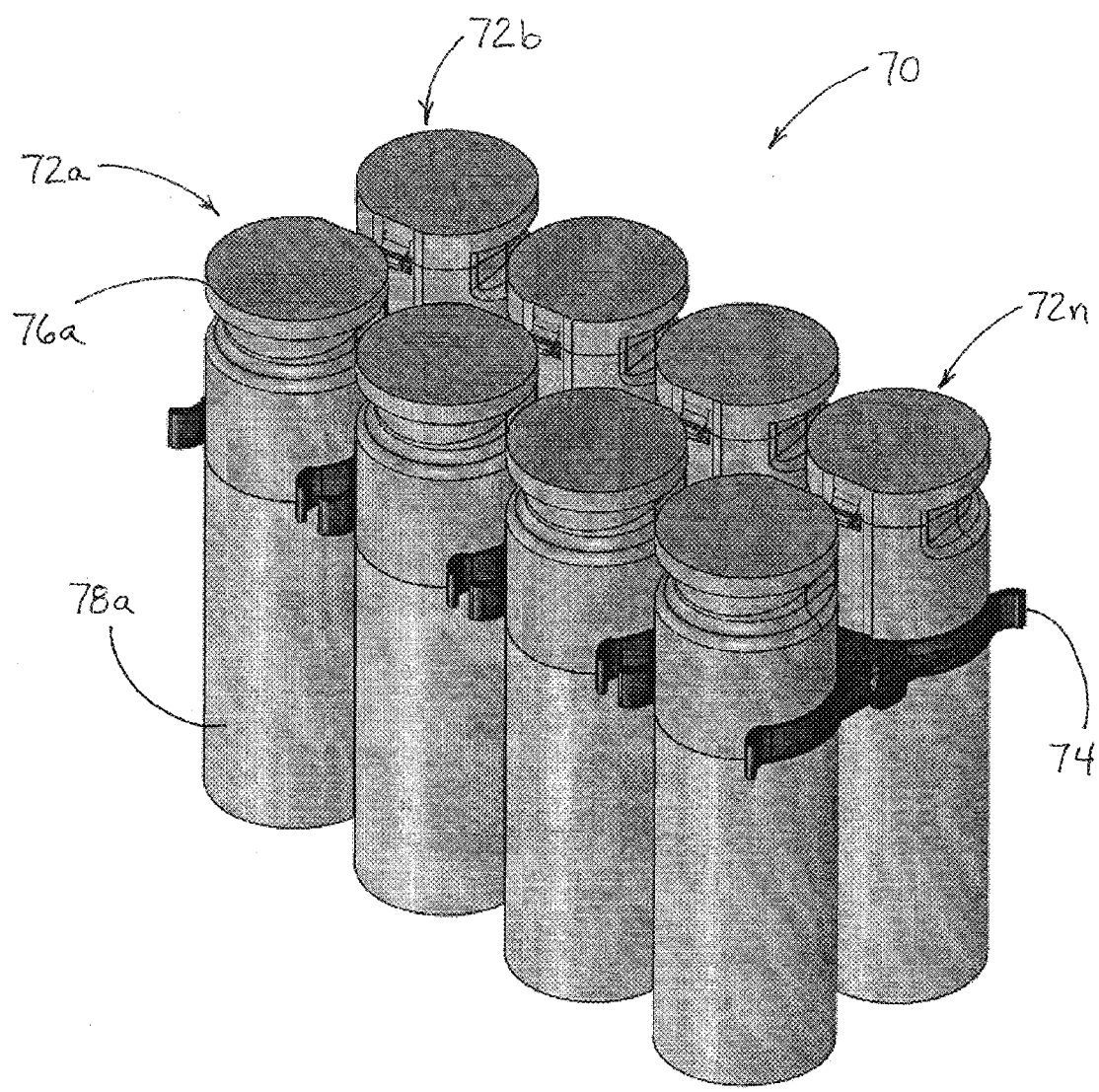
FIG. 4 is a perspective view of a multi-cartridge embodiment of the present invention.

Reference is now made to FIG. 4 for a brief description of a manner in which a number of the container/cartridges of the present invention might be collected into a package. Multi-cartridge pack 70 shown in FIG. 4 is comprised of a plurality of cartridges shown generally as first cartridge 72a, second cartridge 72b, and on through a last cartridge 72n. In the embodiment shown in FIG. 4 there are eight such individual cartridges, although those skilled in the art will recognize that any number of cartridges might be joined together through an appropriately structured clip holder 74. Each cartridge is generally shown to comprise cartridge body 78a and cartridge cap 76a. The caps 76 are shown in FIG. 4 as they would be provided to seal off the opening of the plunger body of the container/cartridge prior to use. An integral hinge may be positioned on one side of each cartridge cap 76 in a manner that allows the user to open the container/cartridges one at a time for use. The used container/cartridges may be removed from the multi-pack and disposed of.

Figure 5A:
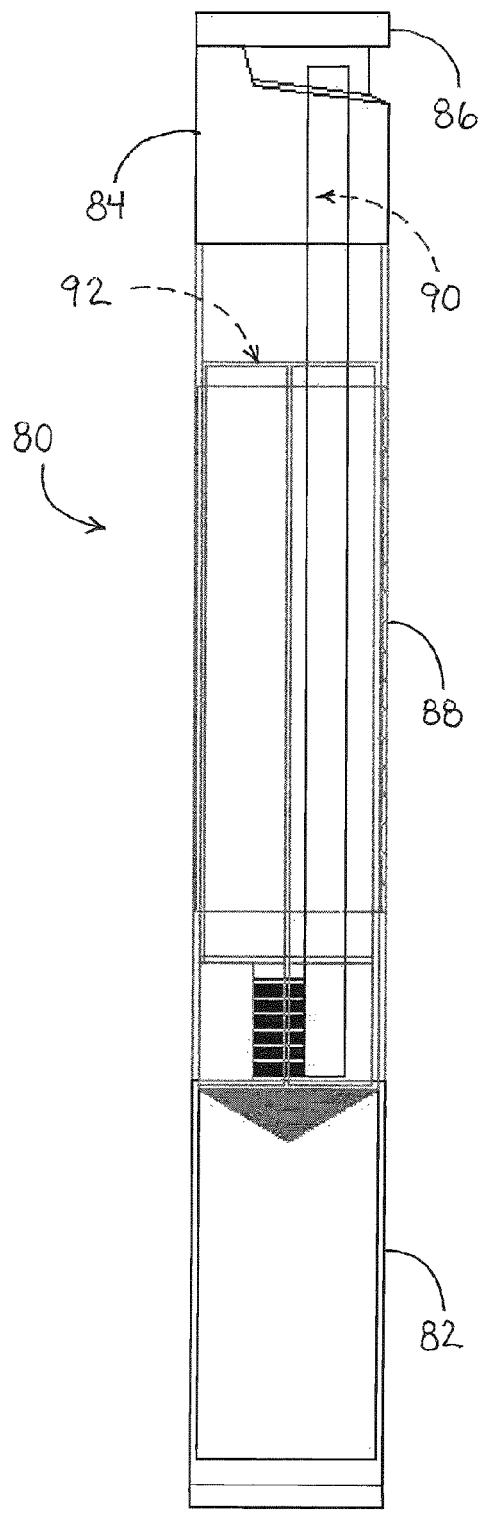
FIGS. 5A and 5B are partial cross-sectional views of an alternate decontaminated cartridge embodiment of the present invention shown in an expanded condition (FIG. 5A) and in a collapsed or activated, but as yet unopened condition (FIG. 5B).
Figure 5B:
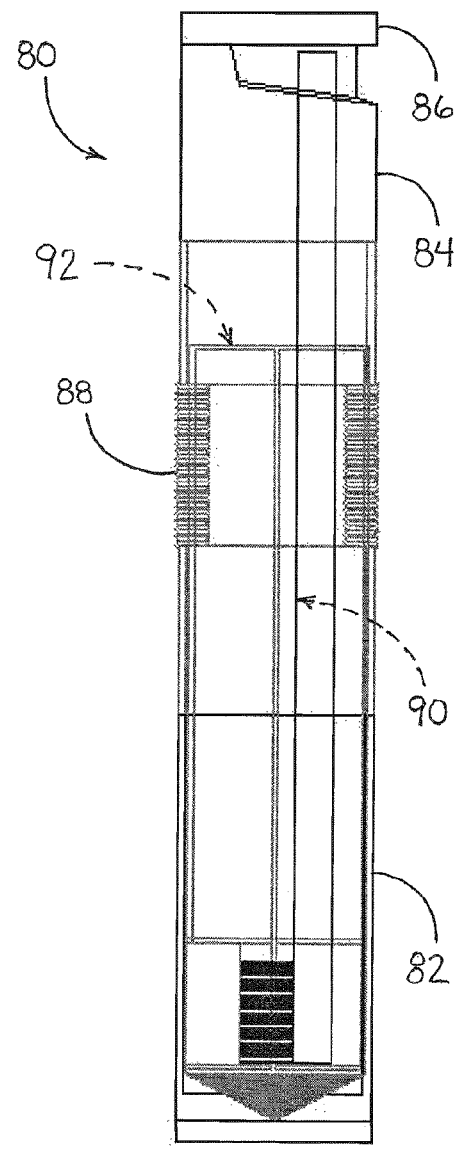

FIGS. 5A and 5B disclose a further alternate embodiment of the present invention constructed basically according to the previous embodiments described above, but with the additional provision of a fully enclosed applicator, or toothbrush. This so called "specialty cartridge" embodiment is provided to assure the maintenance of a clean, uncontaminated state within an enclosed environment surrounding the applicator (toothbrush) from the point of manufacture to the point immediately prior to use. It would be anticipated that the embodiment shown in FIGS. 5A and 5B might be utilized by individuals such as immunocompromised patients who are particularly sensitive to microorganisms, such as bacteria, pathogens, or other contaminants that might otherwise exist on a toothbrush held outside of the enclosed containment.

The specialty cartridge embodiment 80 shown in FIG. 5A is primarily comprised of body base 82 constructed according to the housing and plunger body components of the embodiments described above, as well as body top 84 and integrated cap 86. Toothbrush 90 is fully enclosed within these components and is further surrounded by a connecting, fully extended bellows component 88. An interior structure for maintaining the semi-rigid expanded configuration shown in FIG. 5A may be provided in the form of stabilizing frame 92 included to prevent the unintended collapsing of bellows 88 and thereby the unintended activation of the specialty cartridge embodiment.

FIG. 5B shows the manner in which the decontaminated specialty cartridge embodiment 80 would be fully collapsed as upon intended activation for use according to the methods described above. In this collapsed condition, bellows 88 collapses to allow the dispensing of the liquids/gels as described above, and yet still maintains a full decontaminated enclosure for toothbrush 90 as shown. Use of the toothbrush 90 once activation of the cartridge/container 80 has been accomplished would be by opening cap 86 and removing decontaminated toothbrush 90 from the enclosed containment. In this manner the device may be manufactured within a clean environment with both the disinfectant and the toothpaste integrated into the containment volumes as described above. No multi-use toothbrush would be utilized in this case as a single use brush 90 would be integrated within the container/cartridge 80 as shown. The entire product would typically be disposed of after use, including the toothbrush 90. Because of the decontaminated manufacture of this embodiment of the present invention, the disinfectant liquid in this case may be replaced with a similar quantity of sterile or near sterile water to provide a wetting functionality to the applicator brush without the need for the disinfecting functionality.

Figure 6A:
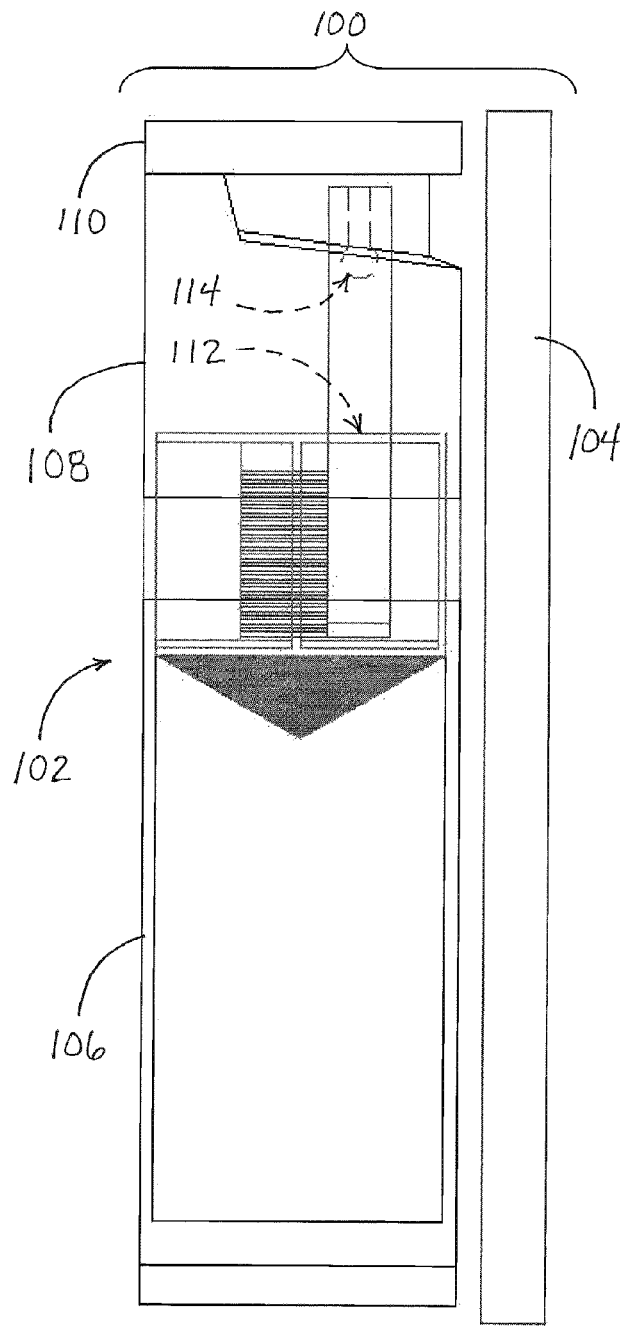
FIGS. 6A and 6B are partial cross-sectional views showing an alternate travel cartridge embodiment of the present invention disclosing an externally positioned handle for the applicator with FIG. 6A representing a side view and FIG. 6B representing an end view.
Figure 6B:
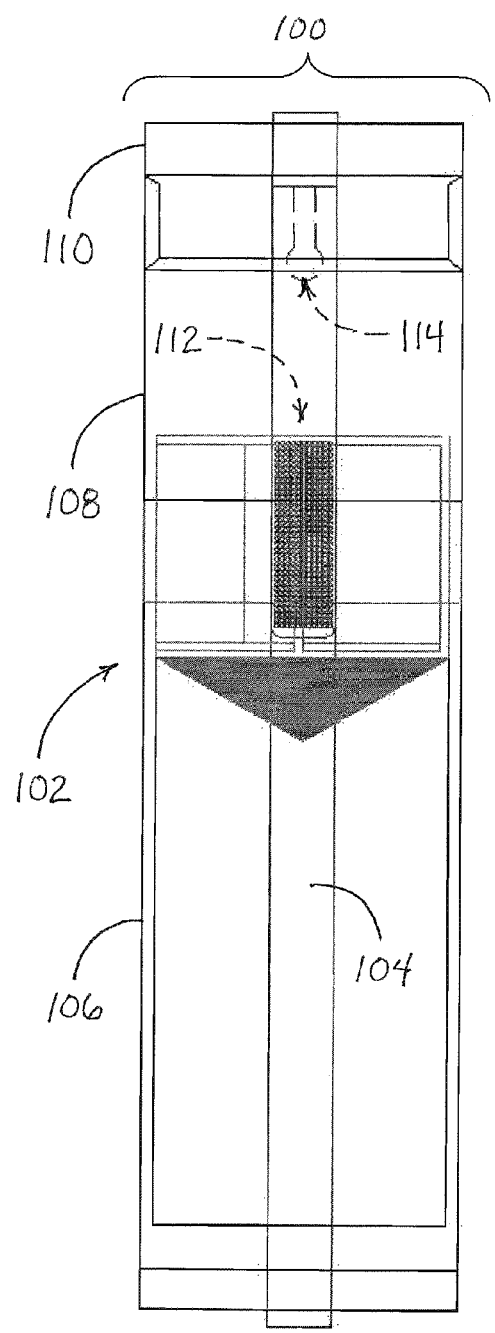

Reference is next made to FIGS. 6A and 6B for a description of a more compact travel embodiment of the cartridge/container of the present invention. FIGS. 6A and 6B show a side view and an end view respectively of the basic manner in which a smaller toothbrush, namely a two-piece toothbrush, may be integrated into the cartridge/container device of the present invention. Travel cartridge 100 being the combination of the cartridge/container 102 and toothbrush handle 104 (shown in a side view in FIG. 6A). This partially schematic view discloses brush top 112 interior to body top 108 and body base 106 of cartridge/container 102. Brush top 112 positioned beneath cap 110 and likewise positioned for connection to brush handle 104 may be removed from a semi-fixed position on the exterior of cartridge component 102. Handle connector 114 is configured on brush top 112 in a manner so as to allow its connection to brush handle 104. Once connected, the same operation of the system of the present invention as described above is accomplished and the combined brush top 112 and brush handle 104 are removed after having been disinfected and supplied with toothpaste. FIG. 6B is an end view showing the manner in which brush handle 104 is positioned on the exterior side of the container cartridge 102 in a kit form.

Figure 7A:
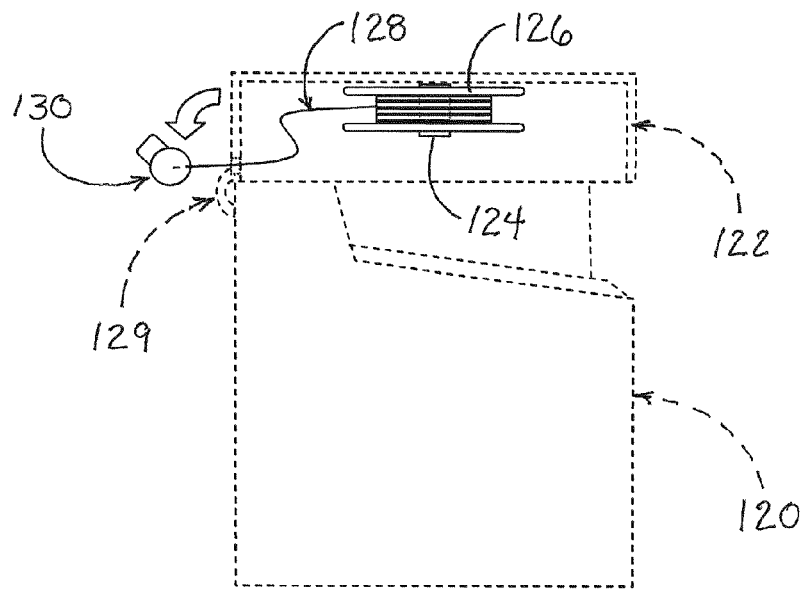
FIGS. 7A-7C are partially schematic detailed plan views of features of the present invention associated with the cartridge cap and the opening of the cartridge body.
Figures 7B, 7C:
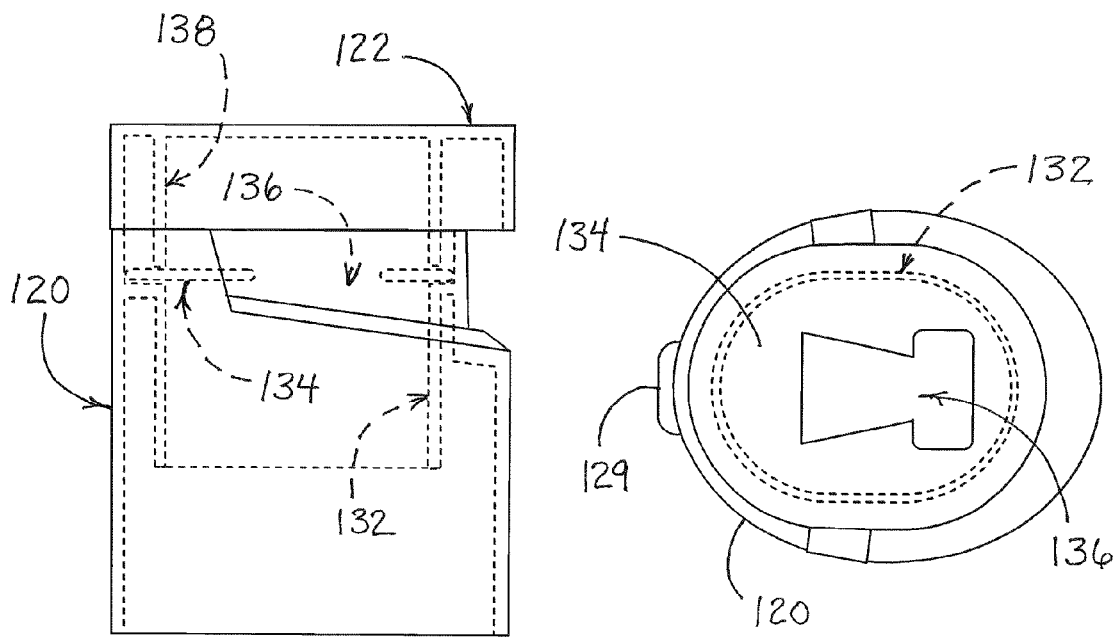

Reference is finally made to FIGS. 7A through 7C for a description of certain detailed features associated with the cap and cartridge body opening of the present invention. FIG. 7A shows the manner of placing a single "dose" of dental floss within the confines of the hinged cap 122 associated with cartridge body top 120. Spool post 124, fixed on the inside of cap 122, retains floss spool 126. A quantity of dental floss 128 is wound on spool 126 and may be dispensed there from for use. Cap hinge 129 may, in the preferred embodiment, provide a sufficient aperture through which the end of floss 128 may be passed to the outside of the cap. Optionally, a floss end tab 130 may be provided to adhere the end of floss 128 to the side of cap 122 where it may be retrieved by the user and pulled from the interior spool 126.

FIGS. 7B & 7C provide detailed views of the internal structures of the cartridge body top 120 and the hinged cap 122 that facilitate the prevention of leakage of liquids/gels from the cartridge during and after use. Cartridge body top may be configured with body top spill wall 132, seen in cross section in FIG. 7B, as well as cartridge top wall 134 defining applicator portal 136 (as generally described above). Hinged cap 122 may likewise be configured with cap spill wall 138 which, when the cap is closed, comes into sealing contact with cartridge top wall 134. In this manner, any liquids/gels that remain within the cartridge after use will be generally confined within the closed cartridge and prevented from leaking out around the external edges of the cap and cartridge body top. These insert walls will keep the disinfecting liquid pool (once discharged from the lower reservoir to the upper portions of the cartridge) from spilling out of the cap should the cartridge be tipped over on its side or turned upside down.

FIG. 7C also shows in a top plan view the manner of configuring applicator portal 136 to best accommodate and seal around the specific type of applicator being utilized. In the example shown, the geometry of applicator portal 136 may be configured to match or nearly match the cross sectional configuration of the applicator. In this manner a better seal is created to maintain the liquids/gels within the cartridge both during and after use. Other geometries will be appropriate for other types of applicators.

As indicated above, an alternate embodiment of the present invention could include a reloadable and/or refillable version of the device. In this alternate preferred embodiment, the containment vessel might be constructed of a somewhat more rigid or dense material, providing a thicker and less fragile walled container. The device might then be repeatedly reused by removing and disposing of the used plunger assembly, refilling the rinse reservoir, and inserting a new, loaded, plunger assembly. With such an embodiment, the user might purchase a single heavily constructed containment vessel and a number of packaged plunger assemblies that may be used in conjunction with the reloadable containment vessel. Understood from the above description of the preferred embodiment of the present invention, the individual plunger assemblies contain relatively less structural plastic material than the more heavily constructed containment vessel. In this manner, significantly less plastic material may be required per use of the device of the present invention.

In general, the device may be constructed of recyclable materials, both with respect to the fully disposable embodiment described above, or the reloadable/refillable embodiment described subsequently. In any event, the plastics typically utilized in conjunction with the manufacture of devices such as the present invention are fully recyclable. Some components of the system of the present invention also lend themselves to being manufactured from recycled plastic material, although it is preferable that some components of the system remain transparent so as to allow the user to confirm the function of the system during use.

Although the above detailed descriptions focus on an oral hygiene application of the present invention, these descriptions are intended to provide support for other uses of the basic capsule concept. In particular, as mentioned briefly above, there is a potential use of such a device for any two-part chemical design wherein the shelf lives and usefulness of the two chemical compounds or solutions are relatively long as compared to the urgency imparted by the chemical mixing process. For instance, two-part epoxy mixtures harden very quickly once mixed but stay liquid indefinitely when held separate. Some chemical compounds require "activation" by secondary compound prior to exhibiting the desired characteristics on an applicator or dispensing surface. The use of an applicator for some compounds (such as paints and the like) might best involve cleaning with a solvent prior to having a second, slightly different compound (color of paint, for example) dispensed onto the applicator. In any of these and other situations, the present invention finds appropriate use.

Although the present invention has been described in terms of the foregoing preferred embodiments, this description has been provided by way of explanation only, and is not intended to be construed as a limitation of the invention. Those skilled in the art will recognize modifications of the present invention that might accommodate specific liquids/gels and specific applicators. Those skilled in the art will further recognize additional methods for modifying the construction of the dispensing container/cartridges to accommodate variations in fluid viscosities, fluid quantities, dynamic pressures, spray velocities, and flow rates. Such modifications, as to structure, orientation, geometry, and even construction, where such modifications are coincidental to the types of applications involved, do not necessarily depart from the spirit and scope of the invention.

We claim:

1. A system for sequentially dispensing multiple fluids onto a removable applicator device, the system comprising:
   (a) a double walled cylindrical container, having a first interior volume defined by first interior walls of the container and a second interior volume defined between exterior and interior walls of the double walled container, the double walled container having a closed base, a double walled mid-section, and a top configured to receive the removable applicator device, the interior and exterior walls of the double walled container further defining a first flow conduit from the first interior volume into the second interior volume near the base of the container and a second flow conduit from the second interior volume into the first interior volume near the mid-section of the container;
   (b) a hollow plunger co-axially positioned within the first interior walls of the double walled cylindrical container, the plunger having a face and the positioning of the plunger defining a first fluid containment volume between the plunger face and the closed base of the double walled container, the hollow plunger further comprising a collapsible walled enclosure formed above the face of the plunger defining a second fluid containment volume, the collapsible walled enclosure having an exit opening generally opposite the plunger face;
   (c) a quantity of a first liquid/gel positioned within the first fluid containment volume; and
   (d) a quantity of a second liquid/gel positioned within the second fluid containment volume;
   wherein movement of the plunger downward into the first fluid containment volume under the influence of the applicator inserted through the top, directs at least a portion of the quantity of the first liquid/gel to be forced outward through the first flow conduit, upward into the second interior volume, inward through the second flow conduit, and into the first interior volume of the double walled container onto the applicator, and wherein further movement of the plunger downward under the influence of the applicator brings the plunger face into contact with the closed base of the container and causes the collapse of the hollow plunger, thereby directing at least a portion of the quantity of the second liquid/gel through the exit opening onto the applicator.

* * * * *